United States Patent [19]
Iijima et al.

[11] Patent Number: 5,989,195
[45] Date of Patent: Nov. 23, 1999

[54] NONCONTACT TONOMETER

[75] Inventors: Hiroshi Iijima; Akinari Takagi, both of Tokyo, Japan

[73] Assignee: Kabushiki Kaisha Topcon, Tokyo, Japan

[21] Appl. No.: 09/084,590

[22] Filed: May 27, 1998

[30] Foreign Application Priority Data

May 28, 1997 [JP] Japan ..................................... 9-138593

[51] Int. Cl.⁶ ........................................................ A61B 5/00
[52] U.S. Cl. .......................... 600/561; 600/399; 600/401; 351/208
[58] Field of Search ..................................... 600/398, 399, 600/401, 561; 351/208, 211, 212

[56] References Cited

U.S. PATENT DOCUMENTS

| | | | |
|---|---|---|---|
| 4,995,393 | 2/1991 | Katsuragi et al. | 600/401 |
| 5,000,181 | 3/1991 | Katsuragi | 600/401 |
| 5,033,841 | 7/1991 | Nishio et al. | 351/212 |
| 5,101,826 | 4/1992 | Katsuragi | 351/208 |
| 5,465,123 | 11/1995 | Iijima | 351/208 |
| 5,644,375 | 7/1997 | Suzuki | 351/211 |
| 5,696,573 | 12/1997 | Miwa | 351/205 |
| 5,708,494 | 1/1998 | Iijima et al. | 351/211 |
| 5,776,061 | 7/1998 | Hayafuji | 600/401 |

*Primary Examiner*—Max Hindenburg
*Assistant Examiner*—Charles Marmor, IV
*Attorney, Agent, or Firm*—Finnegan, Henderson, Farabow, Garrett & Dunner, L.L.P.

[57] ABSTRACT

A noncontact tonometer is provided which is capable of intercepting out-of-axis light of an index beam of light and performing precise alignment. The noncontact tonometer includes an index projecting optical system for projecting an index frontally onto a subject's eye (E) through a nozzle (12) through which gas is also is sprayed upon the eye (E). The index projecting optical system has a projection lens (27) and a diaphragm (23) disposed at a position conjugated to an end surface (F) of the nozzle (12) on the side of the projection lens (27). The diaphragm (23) intercepts rays of light traveling out of an optical axis, and enables precise alignment.

4 Claims, 8 Drawing Sheets

NONCONTACT TONOMETER

BACKGROUND OF THE INVENTION

1. Field of the Invention

This invention relates to a noncontact tonometer comprising position detecting means for detecting a position of an apparatus body of the tonometer with respect to a subject's eye.

2. Description of the Related Art

Conventionally, a noncontact tonometer has been known which deforms (i.e., flattens) the cornea C of a subject's eye E by spraying a fluid, such as an air pulse, from a spraying nozzle N, such as that shown in FIG. 9, onto the cornea C, and measures the intraocular pressure of the eye by receiving rays of light reflected by the flattened cornea C with a light receiving element. In the noncontact tonometer, a positional adjustment of the spraying nozzle N to the cornea C needs to be made, and thus the noncontact tonometer includes alignment detecting means for detecting a relative position (hereinafter, referred to as alignment) of its apparatus body to the eye E. And, an alignment detecting method has been known which comprises steps of projecting an index from front onto the cornea C, then receiving rays of light reflected by the corneal surface, and detecting an alignment state from a position of the reflected image.

However, the noncontact tonometer includes a spraying nozzle N for spraying a fluid which is disposed in front of the cornea C. Thus, an index for detecting alignment needs to be projected through the nozzle. In addition, the diameter of a beam of light to be projected needs to be made as large as possible so that a larger alignment-detectable area can be obtained. Hereinafter, a relationship between the subject's eye E and the diameter of the beam will be described in detail hereinafter with reference to FIG. 10, but the spraying nozzle N is not shown in FIG. 10 for convenience of explanation.

FIGS. 10(a) to 10(c) show an alignment optical system 200. The alignment optical system 200 comprises a half mirror 201, an objective lens 202, and a PSD 203. FIG. 10(a) shows a state where a positional adjustment has been made between the cornea C and the apparatus body; FIG. 10(b) shows a state where disalignment has occurred between a vertex P of the cornea C and the apparatus body; and FIG. 10(c) shows a state where disalignment has occurred between the vertex P of the cornea C and the apparatus body and, simultaneously, the diameter of an index beam of light is small.

As shown in FIGS. 10(a) to 10(c), an index beam of light K, which has been collimated by an index beam projecting optical system (not shown) for projecting an index beam of light, is reflected by the half mirror 201, and then is guided to a surface T of the cornea C. At this time, if the alignment has already been completed, the index beam K projected onto the cornea C is reflected by the surface T so as to form a luminous image R at a position between a vertex P of the cornea C and the curvature center of the cornea C. The reflected index beam passes through the half mirror 201, is then condensed by the objective lens 202, and forms an image R' opposite to the luminous image R at the center of the PSD 203.

In the case where the diameter of the index beam K is sufficiently large (see FIGS. 10(a), 10(b)), if there is no disalignment between the cornea C and the apparatus body, as a matter of course, the beam reflected by the cornea C forms an image on the PSD 203 through the objective lens 202. Even if there is disalignment therebetween, a part of the beam forms an image thereon by returning to its optical path, so that an alignment state can be detected. On the other hand, in the case where the diameter of the index beam K is small (see FIG. 10(c)), if its relative position is largely shifted, the beam reflected by the cornea C is reflected in a direction deviated from its optical path, and thus cannot impinge the objective lens 202. Therefore, the reflected beam does not reach the PSD 203, and an alignment state cannot be detected. In other words, it is desired that the index beam K having a larger width is used which enlarges an alignment detectable area.

Therefore, as shown in FIG. 9, if the beam K passes through the whole area of the inside of the nozzle N, a beam of light K1 out of the optical axis will strike an end surface F of the nozzle N on the side of the objective lens, and the reflected (scattering) light K1' from the end surface F will enter the light receiving element of a detecting optical system. If an element for detecting the centroid position of incident light, such as the PSD 203 shown in FIG. 10, is used as a light receiving element, the beam reflected by the end surface F of the nozzle N acts as a noise which causes the false detection of alignment.

SUMMARY OF THE INVENTION

An object of the present invention is to provide a noncontact tonometer which is capable of detecting precise alignment by intercepting an out-of-axis light beam which causes a noise.

The present invention is characterized in that, in a noncontact tonometer comprising fluid discharging means for discharging a fluid onto the cornea of a subject's eye through a nozzle, corneal deformation detecting means for detecting deformation of the cornea flattened by the fluid, in which an intraocular pressure of the eye is measured according to a signal obtained by the corneal deformation detecting means, the noncontact tonometer further comprises index projecting means for projecting an index from front onto the eye through the inside of the nozzle, and position detecting means for receiving an image of the index reflected by a corneal surface and detecting a position of the cornea in up, down, right, and left directions according to a position of the reflected image, in which the index projecting means includes a projection lens and a diaphragm, disposed at a position conjugated to the end surface of the nozzle on the side of the projection lens, for intercepting a beam of light proceeding to the end surface of the nozzle.

Preferably, the position detecting means includes a PSD as a light receiving element. The noncontact tonometer may further comprise driving means for automatically driving an apparatus body of the tonometer according to information obtained by the position detecting means. Preferably, the diaphragm conjugated to the nozzle has a diameter equal to that of an opening of the nozzle.

DESCRIPTIOIN OF THE PREFERRED EMBODIMENTS

[First Embodiment]

Figure 1:
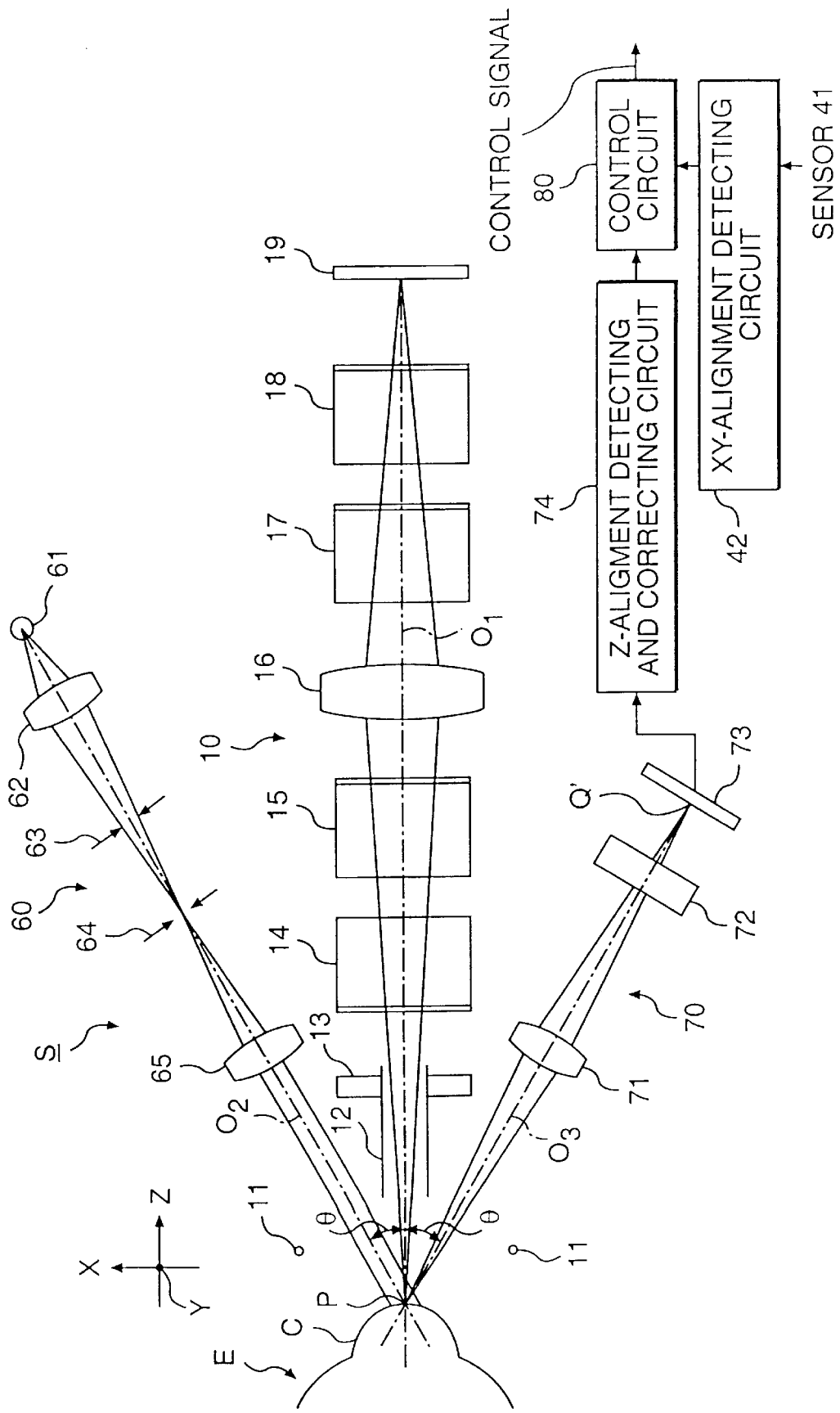
FIG. 1 is a plan view showing the arrangement of optical systems of a noncontact tonometer according to the present invention.
Figure 2:
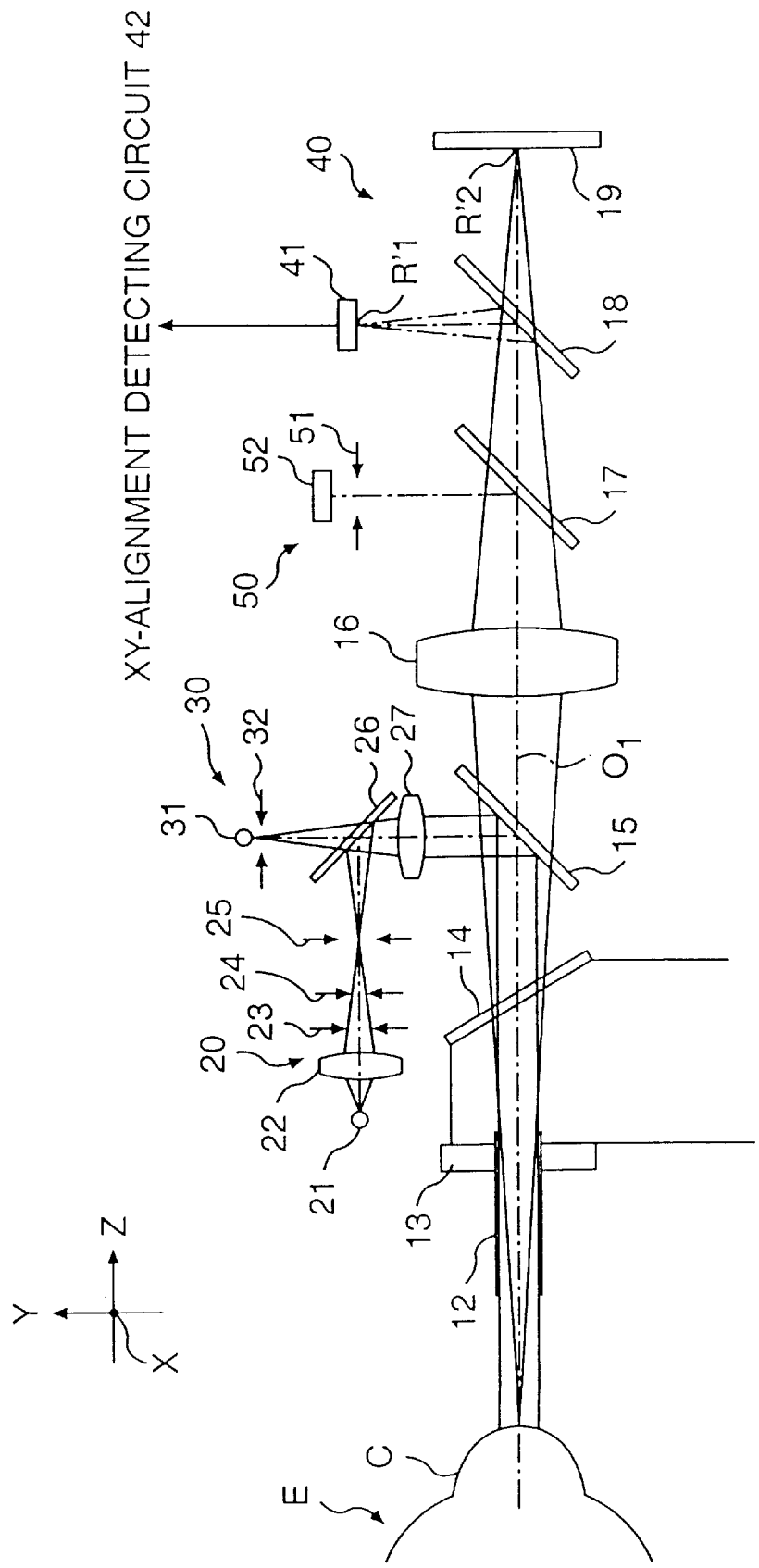
FIG. 2 is a side view showing the arrangement of the optical systems of the noncontact tonometer according to the present invention.

As shown in FIGS. 1 and 2, an apparatus S according to the present invention comprises an eye front observing optical system 10 for observing the front part of a subject's eye E, an XY alignment index projecting optical system (index projecting means) 20 for projecting from front onto the cornea C of the eye E an index beam of light used to detect alignment in an XY-direction, a gaze fixing index projecting optical system 30 for providing a gaze fixing index on which the subject's gaze is fixed, an XY-alignment detecting optical system (position detecting means) 40 for receiving the XY-alignment index light beam reflected by the cornea C and detecting a positional relationship in the XY-direction between the apparatus S and the cornea C, a corneal deformation detecting optical system (corneal deformation detecting means) 50 for receiving the XY-alignment index light beam reflected by the cornea C and detecting an amount of deformation of the cornea C, a Z-alignment index projecting optical system 60 for projecting an index beam of light used for a Z-alignment from an oblique direction onto the cornea, and a Z-alignment detecting optical system 70 for receiving the Z-alignment index light beam reflected by the cornea C from a direction symmetrical with respect to the optical axis of the eye front observing optical system 10 and detecting a positional relationship in the Z-direction between the apparatus S and the cornea C.

The eye front observing optical system 10 comprises a plurality of light sources 11 which are situated on the right and left sides of the subject's eye E and which directly illuminate the front part of the eye E, a gas spraying nozzle 12, an eye front window glass 13, a chamber window glass 14, a half mirror 15, an objective lens 16, half mirrors 17, 18, and a CCD camera 19. Herein, reference character O1 denotes the optical axis of the eye front observing optical system 10.

The image of the front part of the subject's eye E illuminated by the eye front illuminating light sources 11 passes through the inside and outside of the gas spraying nozzle 12, is then transmitted by the eye front window glass 13, the chamber window glass 14 and the half mirror 15, is then transmitted by the half mirrors 17, 18 while being converged by the objective lens 16, and is formed on the CCD camera 19.

The gaze fixing index projecting optical system 30 comprises a light source 31 which is used for a gaze fixing index and emits visible light, a pinhole plate 32. the dichroic mirror 26, the projection lens 27, the half mirror 15, the chamber window glass 14, and the gas spraying nozzle 12.

The gaze fixing index beam emitted from the gaze fixing index light source 31 is collimated by the projection lens 27 via the pinhole plate 32 and the dichroic mirror 26, and is reflected by the half mirror 15, thereafter is transmitted by the chamber window glass 14 and passes through the inside of the gas spraying nozzle 12, and is led to the subject's eye E. A subject gazes fixedly at the gaze fixing index as a gaze fixing target, and the subject's eye is fixed.

The XY alignment index projecting optical system comprises a light source 21 which emits infrared light and is used for XY alignment, a condenser lens 22, a diaphragm 23, an aperture diaphragm 24, a pinhole plate 25, a dichroic mirror 26, a projection lens 27 which is situated on an optical path so as to be focused on the pinhole plate 25, the half mirror 15, the chamber window glass 14, and the gas spraying nozzle 12.

Figure 3:
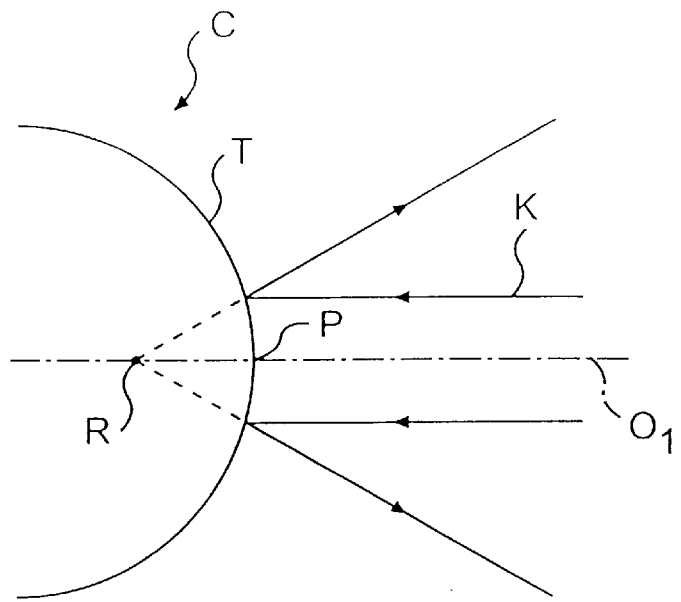
FIG. 3 is an explanatory drawing of reflection of an alignment beam of light projected from front onto the cornea.
Figure 9:
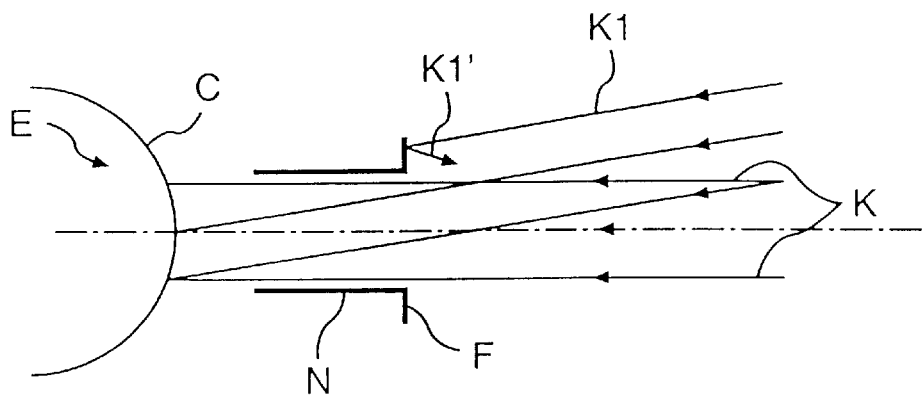
FIG. 9 is an explanatory drawing showing a relationship between the spraying nozzle and the subject's eye.

The infrared light emitted from the XY alignment light source 21 passes through the diaphragm 23 and the aperture diaphragm 24 while being converged by the condenser lens 22, and reaches the pinhole plate 25. The light beam which has passed through the pinhole plate 25 is reflected by the dichroic mirror 26, is then collimated by the projection lens 27 and is reflected by the half mirror 15, thereafter is transmitted by the chamber window glass 14 and passes through the inside of the gas spraying nozzle 12, and, as shown in FIG. 3, is turned into an XY alignment index beam K. In FIG. 3, the XY alignment index beam K is reflected by a corneal surface T so as to form a luminous point image R in a position between a vertex P of the cornea C and the curvature center of the cornea C. Herein, the aperture diaphragm 24 is disposed in a position conjugated to the vertex P with respect to the projection lens 27.

Figure 4A:
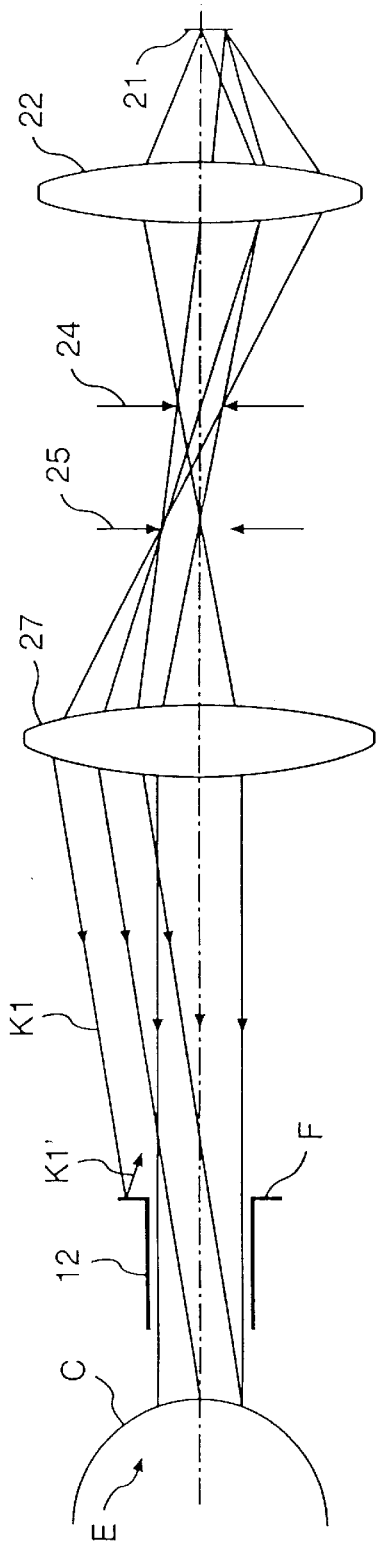
FIG. 4(a) is a side view of an XY alignment index projecting optical system which is not provided with a diaphragm conjugated to an end surface of a spraying nozzle.
Figure 4B:
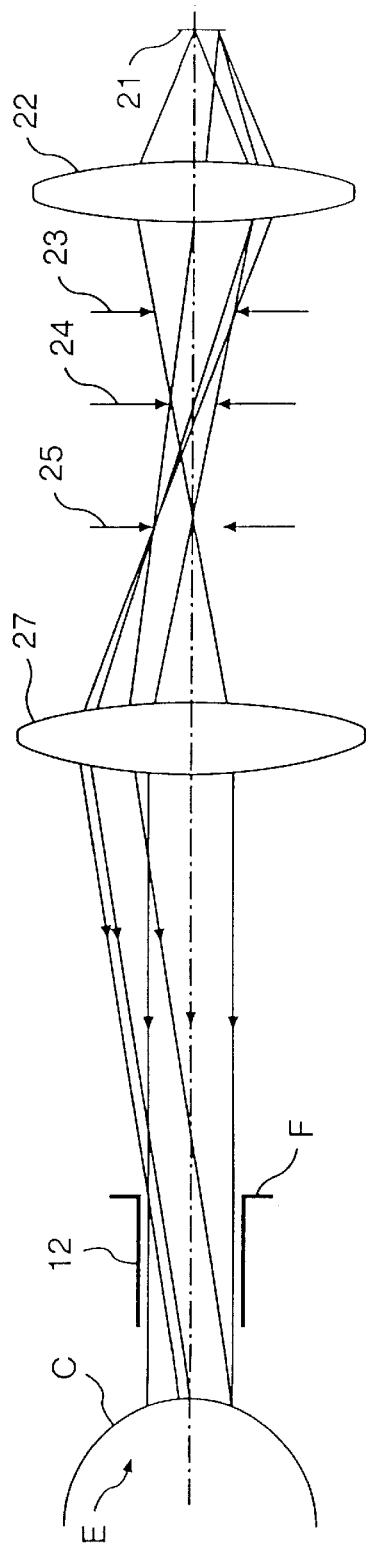
FIG. 4(b) is a side view of an XY alignment index projecting optical system which is provided with the diaphragm conjugated to the end surface of the spraying nozzle.

The diaphragm 23 is disposed in a position conjugated to an end surface F on the side of the objective lens 16 of the gas spraying nozzle 12 with respect to the projection lens 27. A function of the diaphragm 23 will be explained with reference to FIGS. 4(a) and 4(b). FIGS. 4(a) and 4(b) are schematic views of an XY alignment index projecting optical system, in which the dichroic mirror 26 is not shown. In FIG. 4(a) shows a case where it is not provided with the diaphragm 23, and In FIG. 4(b) shows a case where it is provided with the diaphragm 23. As shown in FIG. 4(a), in the case where it is not provided with the diaphragm 23, the light beam which has passed through the center of the pinhole plate 25 passes through the whole inside of the nozzle 12 without being repelled by the end surface F of the nozzle 12, whereas a part of the light beam (an out-of-axis light beam K1) which has passed through the periphery of the pinhole plate 25 is repelled thereby. The beam K1 which has struck the end surface F of the nozzle 12 is scattered and reflected, and a reflected light beam K1' enters a sensor of an XY-alignment detecting optical system (mentioned later). This brings about an error in detection of alignment. Therefore, in order to avoid the error, the diaphragm 23 which serves to cut off or intercept unnecessary light in advance is provided as shown in FIG. 4(b). Thus, the diameter of a projecting light beam can be made larger without generating ghost light, and an alignment detectable area can be made larger. Further, as can be seen in FIG. 4(b), the diaphragm 23 has a diameter equal to that of an opening of the nozzle 12.

The XY alignment detecting optical system 40 comprises the gas spraying nozzle 12, the chamber window glass 14, the half mirror 15, the objective lens 16, the half mirrors 17, 18, a sensor (a light receiving element) 41, and an XY alignment detecting circuit 42.

The light beam which has been projected onto the cornea C by the XY alignment index projecting optical system 20 and has been reflected on a corneal surface T passes through the inside of the nozzle 12, and then is transmitted by the chamber window glass 14 and the half mirror 15. A part of the beam is then transmitted by the half mirror 17, and a part of the transmitted beam part is reflected by the half mirror 18 while being converged by the objective lens 16. The light reflected by the half mirror 18 forms a luminous point image R'1 on the sensor 41. Herein, the sensor 41 is a photosensor capable of detecting a position, such as a PSD. The XY-alignment detecting circuit 42 calculates the positional relationship (in the XY-direction) between the apparatus S and the cornea C by well-known means according to the output of the sensor 41, and then outputs the arithmetic results to an arithmetic control circuit 80.

Figure 5:
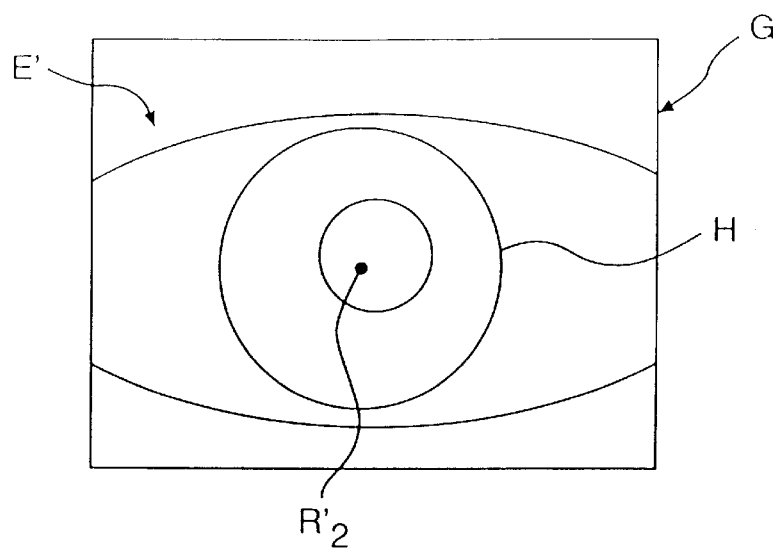
FIG. 5 is an explanatory drawing showing an image of the front part of a subject's eye displayed on the screen of a monitor.

The reflected beam from the cornea C which has been transmitted by the half mirror 18 forms a luminous point image R'2 on the CCD camera 19. The CCD camera 19 outputs an image signal to a monitor unit, and, as shown in FIG. 5, an image E' of the front part of the eye E and the luminous point image R'2 of the XY alignment index beam are displayed on a screen G of the monitor unit. Herein, reference character H denotes an alignment auxiliary mark formed by imaging means (not shown).

The part of the beam reflected by the half mirror 17 is led to the corneal deformation detecting optical system 50 and is led to a sensor 52 through a pinhole plate 51. Herein, the sensor 52 is a photosensor capable of detecting an amount of light, such as a photodiode.

The Z-alignment index projecting optical system 60 comprises a Z-alignment light source 61 for emitting infrared light, a condenser lens 62, an aperture diaphragm 63, a pinhole plate 64, and a projection lens 65 which is situated on an optical path so as to be focused on the pinhole plate 64. Herein, reference character O2 denotes an optical axis of the Z-alignment index projecting optical system 60.

Figure 6:
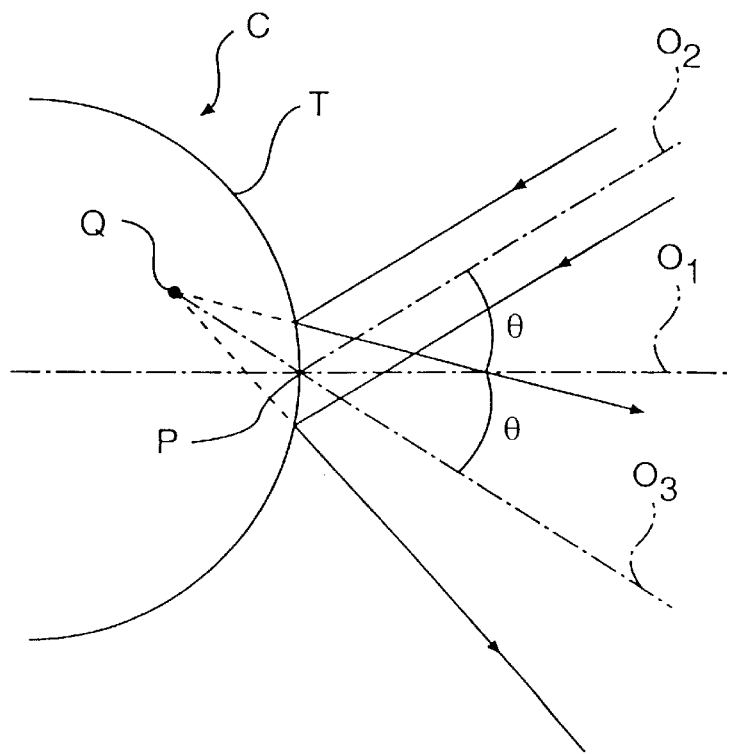
FIG. 6 is an explanatory drawing of reflection of an alignment beam of light projected from an oblique direction onto the cornea.

The infrared light beam emitted from the Z-alignment light source 61 is condensed by the condenser lens 62 and then is led to the pinhole plate 64 through the aperture diaphragm 63. The light beam which has passed through the pinhole plate 64 is collimated and is led to the cornea C by the projection lens 65, as shown in FIG. 6, and is reflected by the corneal surface T so as to form a luminous point image Q. Herein, the aperture diaphragm 63 is in a position conjugated to the corneal vertex P with respect to the projection lens 65.

The Z-alignment detecting optical system 70 comprises an imaging lens 71, a cylindrical lens 72 having a power in a Y-direction, a sensor 73, and a Z-alignment detecting circuit 74. Reference character O3 denotes an optical axis of the Z-alignment detecting optical system 70.

The index light beam projected by the Z-alignment index projecting optical system 60 is reflected by the corneal surface T, is then condensed by the imaging lens 71, and forms a luminous point image Q' on the sensor 73 through the cylindrical lens 72. Herein, the sensor 73 is a photosensor capable of detecting a position, such as a line sensor or a PSD. The information obtained by the sensor 73 is guided to the Z-alignment detecting circuit 74, and the Z-alignment detecting circuit 74 calculates the positional relationship (in the Z-direction) between the apparatus S and the cornea C by well-known means according to the output of the sensor 41, and outputs the arithmetic results to a control circuit 80.

In X-Y plane coordinates, the luminous point image Q is in a position conjugated to the sensor 73 with respect to the imaging lens 71, and in Y-Z plane coordinates, the corneal vertex P is in a position conjugated to the sensor 73 with respect to the imaging lens 71 and the cylindrical lens 72. In other words, since the sensor 73 is in a position conjugated to the aperture diaphragm 63 (in this case, the magnification of an image of the aperture diaphragm 63 is designed to be lower than that of the sensor 73), the light beam reflected by the corneal surface T is effectively made incident upon the sensor 73 even though the cornea C has been shifted in a Y-direction. Also, the same function as this function can be obtained even by projecting a slit beam of light in the Y-direction, although the efficiency becomes lower.

After that, an operator adjusts adjustment by manually moving the apparatus S in the XYZ-directions so that the luminous point image R'2 can come into the alignment auxiliary mark H and can be brought into focus while observing the eye front image E' on a monitor screen shown in FIG. 5. On this occasion, when outputs of the XY-alignment detecting circuit 42 and the Z-alignment detecting circuit 74 are within a predetermined range, the control circuit 80 operates air stream spraying means (not shown) and allows the gas spraying nozzle 12 to spray an air stream onto the cornea C, and the corneal deformation detecting optical system 50 detects an amount of corneal deformation. And, the control circuit 80 calculates the intraocular pressure of the eye E according to an air stream spraying pressure which generates a predetermined amount of corneal deformation. In this way, the control circuit 80 is also used as means for measuring an intraocular pressure.

Further, another construction may also be employed in which an alignment state between the apparatus S and the subject's eye E is detected based on XY-alignment information output by the XY-alignment detecting circuit 42 and Z-alignment information output by the Z-alignment detecting circuit 74, and detection results are displayed on a unit such as a CRT.

[Second Embodiment]

Next, a second embodiment of the present invention will be explained hereinafter. In the first embodiment, an operator adjusts alignment by manually moving the apparatus S in the XYZ-directions. In contrast, in the second embodiment, a driving mechanism (driving means) for moving the apparatus S in the XYZ-directions is provided to automatically adjust alignment.

Figure 7:
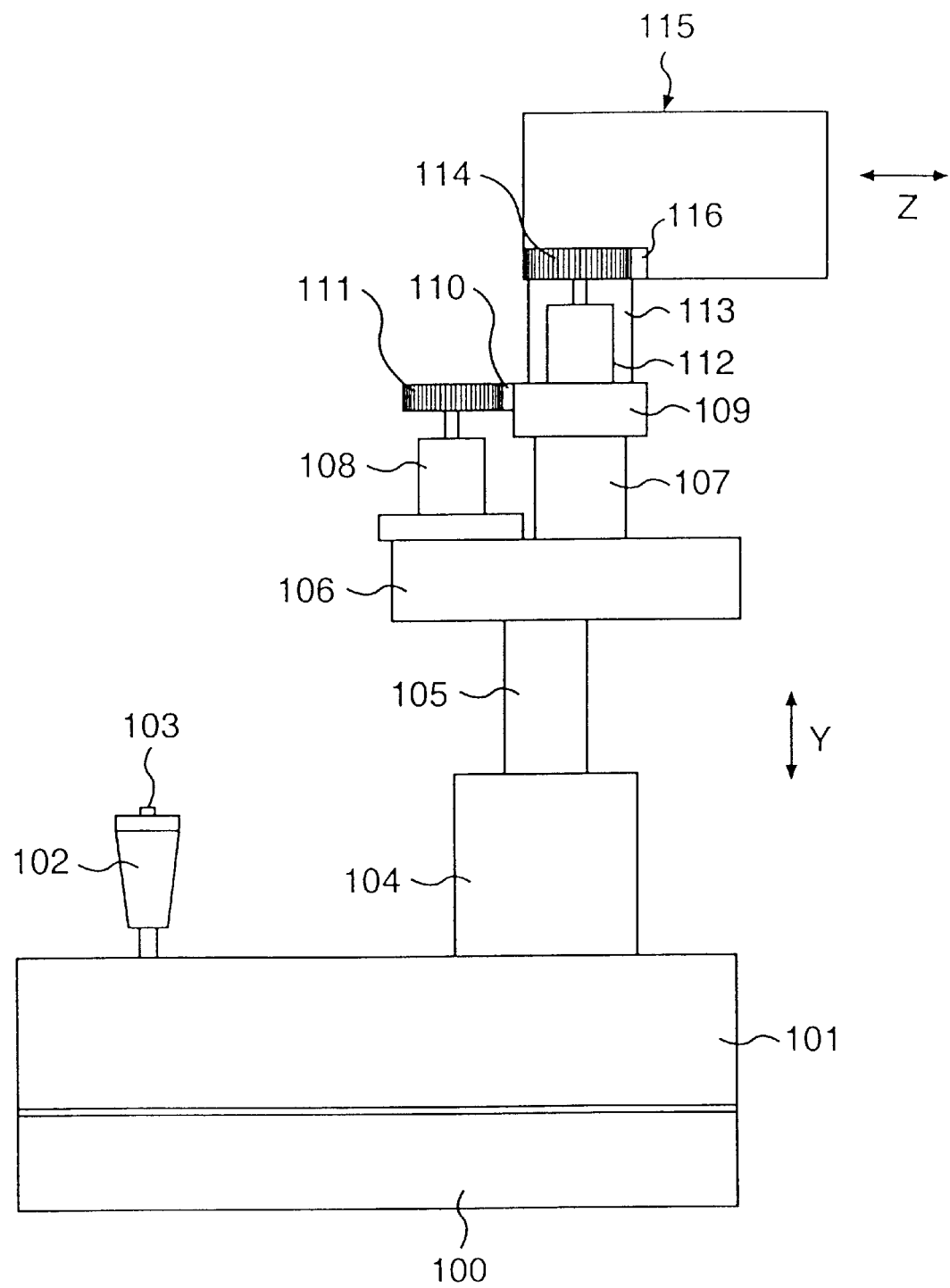
FIG. 7 is a side view of the whole noncontact tonometer according to the present invention.

FIG. 7 is a side view of the whole ophthalmologic apparatus, and reference character 100 denotes a base containing a power source. A stand 101 is attached to the upper part of the base 100 so as to be moved in front, back, right, and left directions by the operation of a control lever 102. The control lever 102 is provided with a manual switch 103 which is used in the case of a manual mode (note that a manual mode is used in the first embodiment). A motor 104 and a supporting column 105 are disposed on and above the stand 101, respectively. The motor 104 is connected to the supporting column 105 by means of a pinion rack (not shown), and the supporting column 105 is moved up and down (in a Y-direction) by the motor 104. A table 106 is attached to the upper end of the supporting column 105.

Figure 8:
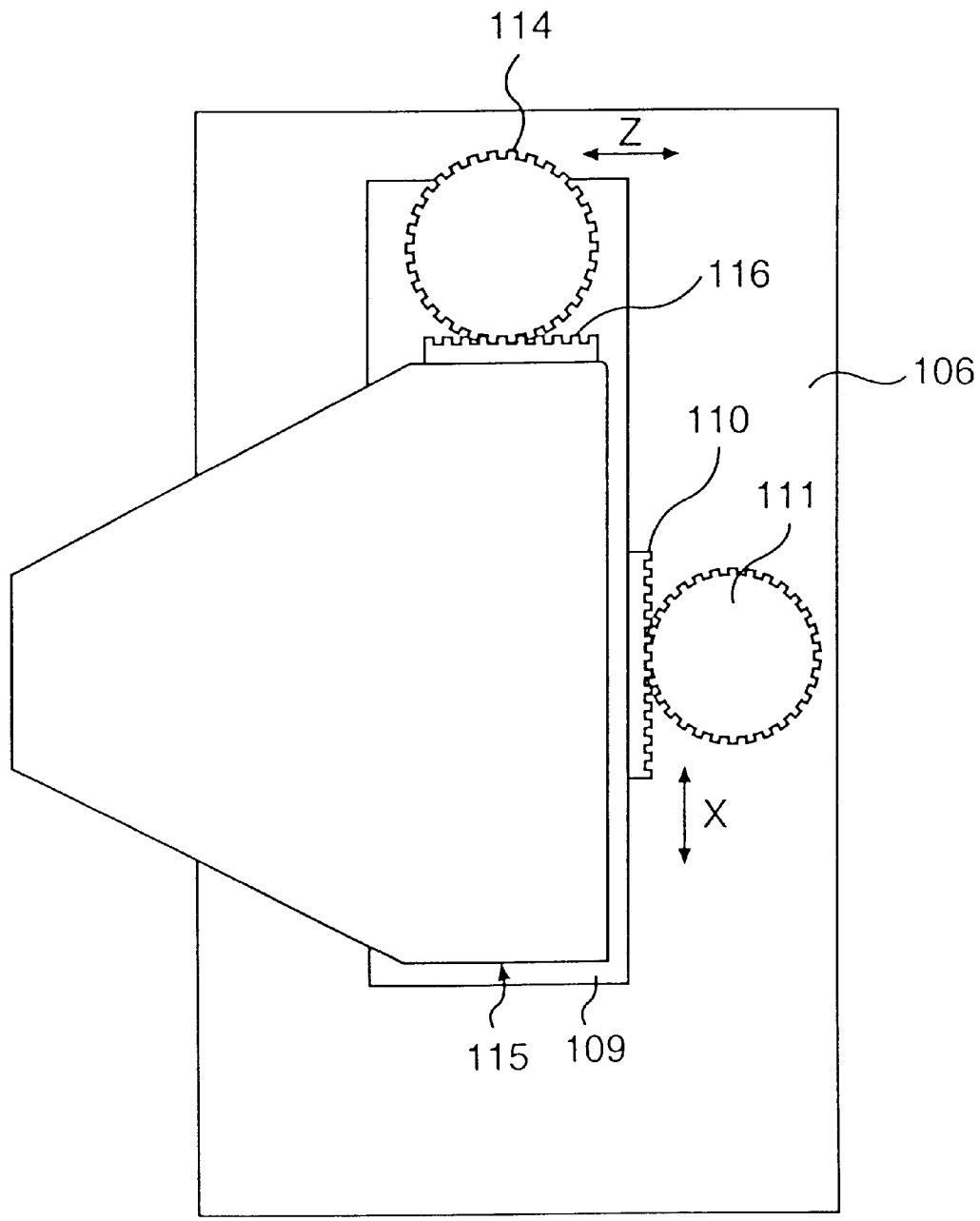
FIG. 8 is a plan view of the essential part of the noncontact tonometer according to the present invention.
Figure 10A:
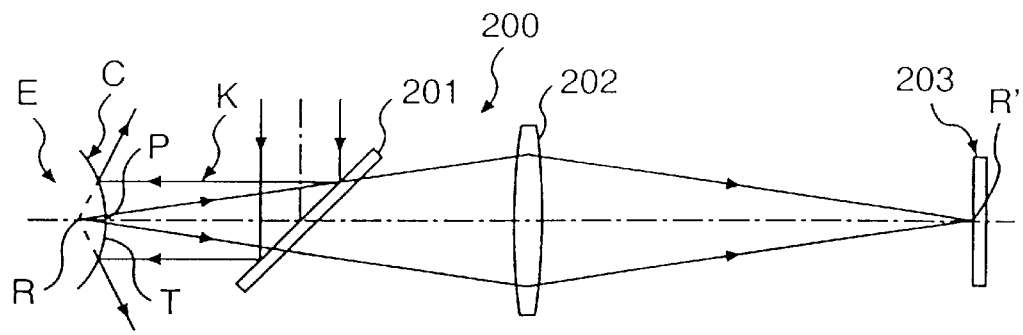
FIGS. 10(a) to 10(c) are explanatory drawings, each showing the diameter of an index beam of light K and the alignment detection area.
Figure 10B:
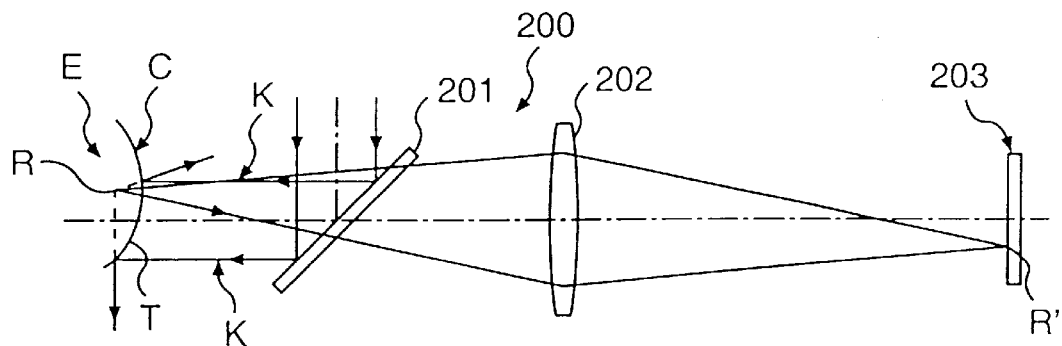
Figure 10C:
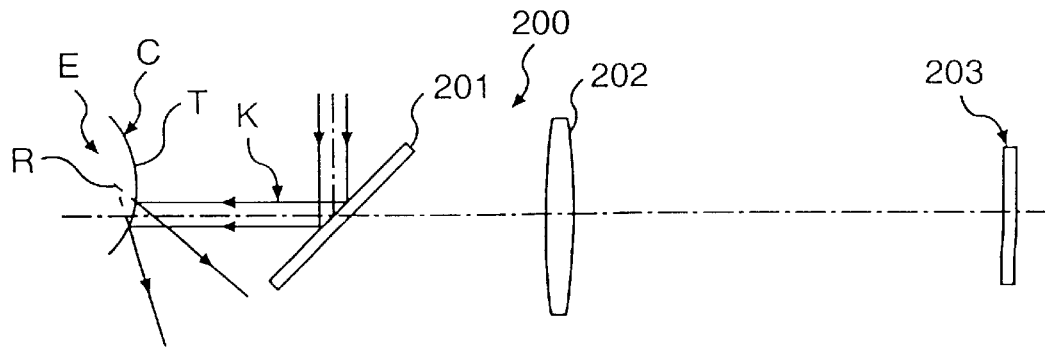

A supporting column 107 and a motor 108 are attached to the table 106. A table 109 is attached to the upper end of the supporting column 107 so that it can slide. As shown in FIG. 8, a rack 110 is attached to the back end of the table 109. A pinion 111 is attached to the power shaft of the motor 108, and the pinion 111 is engaged with the rack 110. A motor 112 and a supporting column 113 are attached to the upper part of the table 109. A pinion 114 is attached to the power shaft of the motor 112. An apparatus body case 115 is attached to the upper part of the supporting column 113 so that it can slide. A rack 116 is attached to the side part of the apparatus body case 115. The rack 116 is engaged with the pinion 114. Herein, inside the apparatus body 115 is disposed the optical system shown in FIG. 1 and FIG. 2.

The motors 104, 108, 112 are controlled by a control signal output by the control circuit 80. The movement in the Y-direction, the movement in the X-direction, and the movement in the Z-direction of the apparatus body 115 are controlled when the control signal is output to the motor 104, the motor 108, and the motor 112, respectively. Thereby, alignment is automatically adjusted.

As explained heretofore, a noncontact tonometer according to the present invention comprises a gas spraying nozzle for guiding a fluid to the cornea C of a subject's eye, fluid discharging means for discharging and spraying a fluid onto the cornea of the eye through the nozzle, a projection lens for guiding an index light beam emitted by an index light source to an path of the inside of the nozzle and projecting the index light beam from front onto the subject's eye, index projecting means including a diaphragm for intercepting a light beam proceeding to an end surface of the nozzle on the side of the projection lens, the diaphragm being in a position conjugated to the end surface of the nozzle with respect to the projection lens, position detecting means for receiving an image of the index light beam reflected by the corneal surface of the eye and detecting a position of the cornea of the eye in up, down, right, and left directions according to a position of the reflected image, corneal deformation detecting means for detecting deformation of the cornea deformed by the fluid, and intraocular pressure measuring means for measuring an intraocular pressure of the eye according to a signal obtained by the corneal deformation detecting means and a gas stream spraying pressure by the fluid discharging means. According to this construction, an alignment detectable area can be made larger, and, in addition, precise alignment can be detected.

Further, when the position detecting means includes a PSD as a light receiving element, alignment can be detected by using a light receiving element having a simpler structure, and alignment can be accurately detected by intercepting out-of-axis light which causes noises.

Further, when the noncontact tonometer comprises driving means for automatically driving an apparatus body according to information obtained by the position detecting means, alignment can be conducted automatically and accurately.

Further, when the diaphragm in a position conjugated to the nozzle has a diameter equal to that of an opening of the nozzle, the index light beam can pass through the whole inside of the nozzle 12, and alignment can be accurately conducted by intercepting out-of-axis light proceeding to the end surface of the nozzle.

What is claimed is:

1. A noncontact tonometer comprising:

fluid discharging means for discharging a fluid through a nozzle onto a cornea of an eye of a subject;

corneal deformation detecting means for detecting deformation of the cornea deformed by the fluid, an intraocular pressure of the eye being measured according to a signal from said corneal deformation detecting means;

index projecting means including a projection lens for projecting an index frontally onto the eye through an inside of the nozzle; and position detecting means for receiving an image of the index reflected by the cornea and detecting a position of the cornea in up, down, right, and left directions according to a position of the reflected index image;

wherein said index projecting means further includes a diaphragm for intercepting rays of light proceeding to an end surface of the nozzle facing a side of said projection lens, said diaphragm being disposed in a position conjugated to said end surface of the nozzle with respect to said projection lens.

2. A noncontact tonometer according to claim 1, wherein a light receiving element of said position detecting means is a PSD.

3. A noncontact tonometer according to claim 2, further comprising driving means for automatically driving an apparatus body of said noncontact tonometer, based on information obtained by said position detecting means.

4. A noncontact tonometer according to claim 1, wherein the diaphragm conjugated to the nozzle has a diameter equal to that of an opening of said nozzle.

* * * * *